(12) United States Patent
Sprenger et al.

(10) Patent No.: US 9,084,805 B2
(45) Date of Patent: Jul. 21, 2015

(54) SIALIC ACID TO SUPPORT THE IMMUNE SYSTEM IN THE ELDERLY

(75) Inventors: Nobert Sprenger, Savigny (CH); Karine Vidal, Lausanne (CH); Christine Cherbut, Pully (CH)

(73) Assignee: Nestec S.A., Vevey (CH)

( * ) Notice: Subject to any disclaimer, the term of this patent is extended or adjusted under 35 U.S.C. 154(b) by 559 days.

(21) Appl. No.: 12/991,589

(22) PCT Filed: May 6, 2009

(86) PCT No.: PCT/EP2009/055444
§ 371 (c)(1),
(2), (4) Date: Jan. 21, 2011

(87) PCT Pub. No.: WO2009/135858
PCT Pub. Date: Nov. 12, 2009

(65) Prior Publication Data
US 2011/0189219 A1  Aug. 4, 2011

(30) Foreign Application Priority Data

May 8, 2008  (EP) .................................. 08155855

(51) Int. Cl.
*A61K 39/385* (2006.01)
*A61K 31/7012* (2006.01)
*A23L 1/30* (2006.01)

(52) U.S. Cl.
CPC ............... *A61K 31/7012* (2013.01); *A23L 1/30* (2013.01); *A23V 2002/00* (2013.01)

(58) Field of Classification Search
None
See application file for complete search history.

(56) References Cited

U.S. PATENT DOCUMENTS

| 6,592,863 | B2 | 7/2003 | Fuchs et al. | |
| 6,787,158 | B1 | 9/2004 | Erdmann et al. | |
| 8,216,616 | B2 * | 7/2012 | Deymes et al. | 424/725 |
| 2003/0212027 | A1 * | 11/2003 | Barbera-Guillem et al. | 514/44 |
| 2005/0096263 | A1 * | 5/2005 | Keay et al. | 514/8 |
| 2005/0201952 | A1 | 9/2005 | Sharma | |
| 2011/0124579 | A1 * | 5/2011 | Sprenger et al. | 514/21.1 |

FOREIGN PATENT DOCUMENTS

| CN | 1547966 | 11/2004 |
| EP | 0291265 | 11/1988 |
| JP | 2048529 | 2/1990 |
| WO | 0137846 | 5/2001 |
| WO | 2005056047 | 6/2005 |

OTHER PUBLICATIONS

Gorog et al. Br. J. exp. Path vol. 61, pp. 490-496, 1980.*
Wang et al ((Am J Clin Nutr, 2007, 85(2):561-569).*
PDRhealth Swallowing difficulties.*
Kornizky et al. Clinical Rheumatlogy vol. 14, No. 4, 2000 Abstract only.*
Rybnikov et al., Immunometabolic effects of N-acetylneuraminic acid in acute hemorrhage, vol. 50, No. 10-11, 2005, pp. 24-27 (abstract)—XP-002508012.
Gorog et al., "Anti-Inflammatory Effect of Sialic Acid," Agents and Actions, vol. 8, Issue 5, (1978), pp. 543-544—XP002508011.
Wang, B., "The role and potential of sialic acid in human nutrition," European Journal of Clinical Nutrition vol. 57, (2003), pp. 1351-1369—XP-009077412.
Iijima, et al., "Novel biological function of sialic acid (N-acetylneuraminic acid) as a hydropgen peroxide scavenger", Federation of European Biochemical Societies, vol. 561, No. 1-3, Mar. 12, 2004, pp. 163-166, XP004495471.
Han, X., et al., "Virus Infection resisting multifunctional beverage," vol. 2005, No. 22, Nov. 24, 2011 (abstract)—XP-002500687.
Miyata, T., "Effect of N-Acetylneuraminic Acid on Respiratory Tract Secretion and Inflammation in the Bronchitic Rabbit," Arch. Int. Pharmacodynamie , vol. 304, Jan. 1, 1990, pp. 277-289, XP000943397.
PCT International Search Report for Application No. PCT/EP2009/055444 with an International Filing Date of May 6, 2009 and a Mailing Date of Aug. 28, 2009, 5 Pages.
Food and Development, vol. 34, No. 8, 1999, pp. 44-46.
Abstract of publication No. JP9278660, XP002508013, 1998.
Abstract of pubication No. JP2048529, XP002508014, Feb. 19, 1990.
Abstract of publication No. JP8119986, XP002508015, 1996.

* cited by examiner

*Primary Examiner* — Gary Nickol
*Assistant Examiner* — Khatol Shahnan Shah
(74) *Attorney, Agent, or Firm* — K&L Gates LLP

(57) ABSTRACT

The present invention generally relates to the field of the immune system, in particular to strengthening the immune system of the elderly. One embodiment of the present invention relates to the use of a food product enriched with sialic acid for the preparation of a composition to strengthen the immune system.

16 Claims, 2 Drawing Sheets

SIALIC ACID TO SUPPORT THE IMMUNE SYSTEM IN THE ELDERLY

The present invention generally relates to the field of the immune system, in particular to strengthening the immune system of the elderly. One embodiment of the present invention relates to the use of a food product enriched with sialic acid for the preparation of a composition to strengthen the immune system in the elderly.

During the ageing process the immune functions decline, a phenomenon that affects every human being as well as animals. This is manifested by an increased susceptibility to infections with increased morbidity and mortality.

For example, the age-related changes in the immune system include changes in T cell subsets, with decline in naïve T cells and accumulation of memory T cells, resulting in a decline of T cell function. Similarly, primary antibody responses in aged humans are often weak and short-lived with lower affinity. Hence, the immune system of the elderly is generally less capable of defending the body against external challenges.

A weakened immune system in aged subjects results in a greater risk for infections and in an increased severity of infections compared to younger adults.

Presently, it is successfully attempted to reduce this increased risk for infections by vaccination, although vaccines generally do not work as well in the immune system of older adults. Typical vaccinations used today include vaccinations for diseases such as influenza, pneumonia, hepatitis B, tuberculosis, diphtheria and tetanus.

However, there remains a need in the art for an alternative tool to strengthen the body's immune defence.

The present inventors have addressed this need.

Consequently, it was the object of the present invention to provide the art with a composition that is available to everybody that can be administered without the risk of unwanted side effects, that is inexpensive and that can be used to strengthen the immune system of elderly people.

The present inventors were surprised to see that they could achieve this object by a use in accordance with claim 1.

Sialic acids (SiAc) are a family of charged nine carbon monosaccharides derived from neuraminic acid (NeuAc) and including NeuAc. NeuAc is the only sialic acid normally formed in humans. In other vertebrates, for example N-glycolylneuraminic acids (NeuGc) are also present.

Today, sialic acids are frequently used in the field of infant nutrition. For example, a possible involvement of SiAc in the cognitive development of infants was summarized by Wang (Wang, B. and Brand-Miller, J. (2003) Eur. J. Clin. Nutr. Nov; 57(11):1351-69). Briefly, studies comparing breast-fed and formula-fed infants demonstrate that a higher NeuAc content of breast milk compared to a normal infant formula correlates with an increased NeuAc content of infants saliva and brain. However, behavioural effects of NeuAc supplementation in humans are not available. Nevertheless it is speculated that supplementation of cows milk with NeuAc would provide the cows milk with human milk attributes, which might have an impact on brain development of children.

Natural sources rich in NeuAc, are, e.g., human milk, elephant milk, Indian buffalo milk, meat, eggs and fish.

The present inventors have now found, that sialic acid can not only be successfully administered to infants, but is especially effective in strengthening the immune system of the elderly.

The administrations of the composition of the present invention to aged animals lead to an improved cell-mediated immune response as measured by delayed-type hypersensitivity. Concomitantly, the expression of genes encoding for anti-inflammatory molecules or for molecules involved in the defence against oxidative damage were increased in the liver of animals fed with the composition of the present invention as compared to the control group.

Without wishing to be bound by theory the inventors presently assume that the improved immune response might be explained by decreased inflammation and oxidative damage found in liver, which seem to increase with age and can be decreased upon administration of a said sialic acid enriched composition.

It would be preferred if N-acetylneuraminic acid could be used for this purpose, since it is the only sialic acid that is also naturally formed in humans.

P. Görög et al, describe and anti-inflammatory effect of sialic acid (Agents and Actions, vol. 8, no. 5, 1987, 543-545).

WO 2005/056047 describes the use of sialic acid and its analogues as anti-inflammatory agents.

JP2048529A discloses that N-acetylneuraminate (I) has I-type allergy inhibiting effect.

However, administrating N-acetylneuraminic acid as such leads to a very fast 'acute' uptake and systemic increase in N-acetylneuraminic acid triggering a fast reestablishment of circulating N-acetylneuraminic acid levels by higher excretion into urine.

It would hence be desirable to provide N-acetylneuraminic acid in a form that avoids the generation of a N-acetylneuraminic acid peak and the resulting increased excretion of N-acetylneuraminic acid.

It was hence the object of the present invention to improve the state of the art and to provide a natural immune boosting agent that remains bioavailable for longer periods of time and is in particular beneficial for the elderly.

The inventors achieved this object by the subject matter of the independent claims. The dependant claims further develop the present invention.

Consequently, one embodiment of the present invention is a composition containing a protein fraction comprising N-acetylneuraminic acid bound to a threonine rich peptide/protein backbone for treating or preventing disorders linked to an altered immune system.

The present invention also relates to the use of a composition containing a protein fraction comprising N-acetylneuraminic acid bound to a threonine rich peptide/protein backbone for the preparation of a composition to treat or prevent disorders linked to an altered immune system.

Threonine rich means that the threonine content is higher than the average threonine abundance in the human protein mass. For example, the threonine content may be increased by at least 10% compared to the average threonine abundance in the human protein mass.

Thus threonine may account for at least 6.3 mol-% of the amino acids in the protein fraction.

For example, threonine may be present in an amount of between about 8 and 22% of the total number of amino acids.

The protein fraction may further comprise about 7 to 25% by mass N-acetylneuraminic acid.

N-acetylneuraminic acid may be provided in a glycan bound form. For example N-acetylneuraminic acid may be provided in a form bound to glycoproteins and/or proteoglycans.

According to a particular preferred embodiment of the present invention, the protein fraction comprises N-acetylneuraminic acid (NeuAc) that is characterized by a threonine rich peptide/protein backbone (between 8 and 22% of total number of amino acids) and a NeuAc content of 7 to 25% by mass.

N-acetylneuraminic acid may be provided in the form of an oligosaccharide ingredient, for example, which comprises glycosylated amino acids and peptides of the general formula $R_n Sac_m$ where R is an amino acid residue, Sac is a monosaccharide selected from the group comprising N-acetylneuraminic acid, N-acetyl galactosamine and galactose, n has a value between 1 and 10 with the proviso that if n has the value 1 R is a threonine residue or a serine residue and if n has a value between 2 and 10 the peptide contains at least one threonine or serine residue, m has a value between 2 and 4 and at least 15 mol % of the ingredient is N-acetyl-neuraminic acid.

Preferably n has a value between 1 and 3 and m has a value of 3 or 4.

The ingredient contains at least 15 mol % sialic acid as part of a saccharide chain linked to the hydroxyl group of threonine or serine. The sialic acid may form part of the chain or may itself be a substituent of a monosaccharide unit in the chain.

Preferably, the oligosaccharide ingredient contains the following monosaccharides:—

| Compound | mol % |
| --- | --- |
| N-acetyl galactosamine (GalNAc) | 20-25 |
| galactose (Gal) | 20-25 |
| N-acetyl-neuraminic acid (NeuAc) | 40-17.5 |

The oligosaccharide ingredient may contain from 20 to 25 mol % of a mixture of serine and threonine.

The oligosaccharide ingredient may contain the following glycosylated amino acids or peptides:—

NeuAc-α-2,3-Gal-β-1,3-(NeuAc-α-2,6-)-GalNAc-$R_n$
NeuAc-α-2,3-Gal-β-1,3-GalNAc-$R_n$
Gal-β-1,3-(NeuAc-α-2,6-)-GalNAc-$R_n$
Gal-β-1,3-GalNAc-$R_n$

The oligosaccharide ingredient of the invention may be produced by the hydrolysis of CGMP using an exoprotease and an endoprotease either together or sequentially to obtain a mixture of free amino acids and peptides with a chain length between 2 and 10 and subjecting the hydrolysed mixture to nanofiltration so as to retain the fraction having a molecular weight between 1000 and 2000 Daltons.

CGMP itself is a by-product of cheese-making in which whole milk is treated with the enzyme rennin to precipitate the casein. In this process, CGMP is cleaved from K casein and remains in solution with the whey proteins. This product is known as sweet whey. The CGMP may be separated from the whey proteins by any process known in the art. A suitable process is described in European Patent No. 986312.

Without being bound by theory the inventors suppose that a protein fraction comprising N-acetylneuraminic acid bound to a threonine rich peptide/protein backbone, for example glycan bound N-acetylneuraminic acid, is advantageous over free N-acetylneuraminic acid because of the following reasoning. Free N-acetylneuraminic acid leads to a very fast 'acute' uptake and systemic increase in N-acetylneuraminic acid triggering a fast reestablishment of circulating N-acetylneuraminic acid levels by higher excretion into urine. A protein fraction comprising N-acetylneuraminic acid bound to a threonine rich peptide/protein backbone avoids this. For example, glycan bound N-acetylneuraminic acid reaches all gut segments leading (i) to a slow 'chronic' N-acetylneuraminic acid uptake all along the gut including lower small intestine and colon and (ii) to a stimulation of the beneficial gut microbiota. The beneficial gut microbiota, such as certain bifidobacteria, cleave N-acetylneuraminic acid from the backbone, e.g. the glycan backbone, aiding in lower gut N-acetylneuraminic acid uptake and are then able to profit themselves from the backbone, e.g., the glycan backbone, which is seen in an additional immune boosting effect for the host by the beneficial microbiota. Thus a synergistic benefit of N-acetylneuraminic acid bound to a threonine rich peptide/protein backbone, e.g., glycan bound N-acetylneuraminic acid, over free N-acetylneuraminic acid is seen.

The composition may be to be administered to the elderly.

The present invention also relates to the use of N-acetylneuraminic acid for the preparation of a composition to strengthen the immune system in the elderly.

The present invention further relates to the use of N-acetylneuraminic acid for the preparation of a composition for treating or preventing disorders linked to an altered immune system.

An altered immune system may be a dysregulation of the immune system, such as a noted decline in cell-mediated immune response concomitant with an increased humoral immune dysfunction, as it often occurs in the elderly.

This may result in a lower response to vaccines. The composition of the present invention may be used for producing a vaccine response stimulating effect. Consequently, it may be used to increase the effects of vaccination.

Typical vaccinations that can be made more effective by the composition of the present invention are vaccinations for diseases such as influenza, pneumonia, hepatitis B, tuberculosis, diphtheria and tetanus.

The composition of the present invention may therefore be co-administered with a vaccine. Co-administration includes for the purpose of the present invention the administration of the composition of the present invention from three months before the vaccination period to three months after the vaccination period.

Preferably, is the composition of the present invention to be administered during the vaccination period.

The present invention hence relates also to a composition containing a protein fraction comprising N-acetylneuraminic acid bound to a threonine rich peptide/protein backbone to be co-administered with a vaccine against influenza, hepatitis B, tuberculosis, diphtheria or tetanus for preventing influenza, hepatitis B, tuberculosis, diphtheria or tetanus, respectively.

A subject is considered as "elderly" if it has surpassed the first half of its average expected lifespan in its country of origin, preferably, if it has surpassed the first two thirds of the average expected lifespan in its country of origin, more preferably if it has surpassed the first three quarters of the average expected lifespan in its country of origin, most preferred if it has surpassed the first four fifths of the average expected lifespan in its country of origin.

The composition may be administered to humans or animals, in particular pets, companion animals and/or livestock.

The present invention also relates to a composition enriched with N-acetylneuraminic acid.

N-Acetylneuraminic acid has the following synonyms and abbreviations: o-Sialic acid; 5-Acetamido-3,5-dideoxy-D-glycero-D-galacto-2-nonulosonic acid; 5-Acetamido-3,5-dideoxy-D-glycero-D-galactonulosonic acid; Aceneuramic acid; N-acetyl-neuraminate; N-Acetylneuraminic acid; NANA, and Neu5Ac.

The composition of the present invention may be a nutritional composition, a nutraceutical, a drink, a food additive or a medicament. A food additive or a medicament may be in the form of tablets, capsules, pastilles or a liquid for example. Food additives or medicaments are preferably provided as sustained release formulations, allowing a constant N-acetylneuraminic acid supply for prolonged times.

The composition is preferably selected from the group consisting of milk powder based products; instant drinks; ready-to-drink formulations; nutritional powders; nutritional liquids; milk-based products, in particular yoghurts or ice cream; cereal products; beverages; water; coffee; cappuccino; malt drinks; chocolate flavoured drinks; culinary products; soups; topical creams; suppositories; tablets; syrups; and formulations for transdermal applications.

Milk may be any milk obtainable from animal or plant sources and is preferably cows milk, human milk, sheep milk, goat milk, horse milk, camel milk, rice milk or soy milk.

Instead of milk, also milk derived protein fractions or colostrum may be used.

The composition may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and antimicrobials. It may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like. Further, it may contain an organic or inorganic carrier material suitable for oral or enteral administration as well as vitamins, minerals trace elements and other micronutrients in accordance with the recommendations of Government bodies such as the USRDA.

For example, the composition may contain per daily dose one or more of the following micronutrients in the ranges given:—300 to 500 mg calcium, 50 to 100 mg magnesium, 150 to 250 mg phosphorus, 5 to 20 mg iron, 1 to 7 mg zinc, 0.1 to 0.3 mg copper, 50 to 200 μg iodine, 5 to 15 μg selenium, 1000 to 3000 μg beta carotene, 10 to 80 mg Vitamin C, 1 to 2 mg Vitamin B1, 0.5 to 1.5 mg Vitamin B6, 0.5 to 2 mg Vitamin B2, 5 to 18 mg niacin, 0.5 to 2.0 μg Vitamin B12, 100 to 800 μg folic acid, 30 to 70 μg biotin, 1 to 5 μg Vitamin D, 3 to 10 μg Vitamin E.

The composition of the present invention may contain a protein source, a carbohydrate source and/or a lipid source.

Any suitable dietary protein may be used, for example animal proteins (such as milk proteins, meat proteins and egg proteins); vegetable proteins (such as soy protein, wheat protein, rice protein, and pea protein); mixtures of free amino acids; or combinations thereof. Milk proteins such as casein and whey, and soy proteins are particularly preferred. Very positive results for the purpose of the present invention were achieved when the protein fraction comprised threonine in an amount of between about 8 and 22% of the total number of amino acids of the protein fraction.

If the composition includes a fat source, the fat source more preferably provides 5% to 40% of the energy of the formula; for example 20% to 30% of the energy. DHA may be added. A suitable fat profile may be obtained using a blend of canola oil, corn oil and high-oleic acid sunflower oil.

A source of carbohydrates may more preferably provide between 40% to 80% of the energy of the composition. Any suitable carbohydrate may be used, for example sucrose, lactose, glucose, fructose, corn syrup solids, maltodextrins, and mixtures thereof.

The composition of the present invention may be used to treat or prevent alterations of the immune system and/or to improve altered cell-mediated and humoral immune responses.

The alterations of the immune system may be selected from the group consisting of infections, in particular bacterial, viral, fungal and/or parasite infections; autoimmune-like diseases; innate defence disorders, for example NK cell deficiencies, phagocyte deficiencies, such as leukocyte adhesion deficiency, cyclic neutropenia; and combinations thereof. Autoimmune-like diseases include autoimmune diseases.

The composition of the present invention may also be used to treat or prevent infectious diseases. N-acetylneuraminic acid will for example strengthen the body's immune system which in turn will help to combat infections.

The immune boosting effect of the composition may further be enhanced by the addition of at least one further immune boosting agent.

The composition may also comprise a probiotic microorganism and/or a prebiotic such as for example fructooligosaccharides, galactosyloligosaccharides, pectins and/or hydrolysates thereof.

"Probiotic" means microbial cell preparations or components of microbial cells with a beneficial effect on the health or well-being of the host. (Salminen S, Ouwehand A. Benno Y. et al "Probiotics: how should they be defined" Trends Food Sci. Technol. 1999:10 107-10).

All probiotic micro-organisms may be used in accordance with the present invention. Preferably, they are selected from the group consisting of *Bifidobacterium, Lactobacillus, Streptococcus* and *Saccharomyces* or mixtures thereof, in particular selected from the group consisting of *Bifidobacterium longum, Bifidobacterium lactis, Lactobacillus acidophilus, Lactobacillus rhamnosus, Lactobacillus paracasei, Lactobacillus johnsonii, Lactobacillus plantarum, Lactobacillus salivarius, Enterococcus faecium, Saccharomyces boulardii* and *Lactobacillus reuteri* or mixtures thereof, preferably selected from the group consisting of *Lactobacillus johnsonii* (NCC533; CNCM I-1225), *Bifidobacterium longum* (NCC490; CNCM I-2170), *Bifidobacterium longum* (NCC2705; CNCM I-2618), *Bifidobacterium lactis* (2818; CNCM I-3446), *Lactobacillus paracasei* (NCC2461; CNCM I-2116), *Lactobacillus rhamnosus* GG (ATCC53103), *Lactobacillus rhamnosus* (NCC4007; CGMCC 1.3724), *Enterococcus faecium* SF 68 (NCIMB101415), and mixtures thereof.

The composition of the present invention may further comprise a pain relieving agent, a stabilizing agent, a flavouring agent, a colouring agent, a lubricant, and/or a prebiotic.

Prebiotics are in particular preferred if the composition comprises probiotics, since the presence of probiotics and prebiotics produces a synergistic effect.

"Prebiotic" means food substances that promote the growth of probiotics in the intestines. They are not broken down in the stomach and upper intestine or absorbed in the GI tract of the person ingesting them, but they are fermented by the gastrointestinal microflora and/or by probiotics. Prebiotics are for example defined by Glenn R. Gibson and Marcel B. Roberfroid, Dietary Modulation of the Human Colonic Microbiota: Introducing the Concept of Prebiotics, J. Nutr. 1995 125: 1401-1412.

The prebiotics that may be used in accordance with the present inventions are not particularly limited and include all food substances that promote the growth of probiotics in the intestines. Preferably, they may be selected from the group consisting of oligosaccharides, optionally containing fructose, galactose, mannose; dietary fibers, in particular soluble fibers, soy fibers; inulin; or mixtures thereof. Preferred prebiotics are fructo-oligosaccharides, galacto-oligosaccharides, isomalto-oligosaccharides, xylo-oligosaccharides, oligosaccharides of soy, glycosylsucrose, lactosucrose, lactulose, palatinose-oligosaccharides, malto-oligosaccharides, gums and/or hydrolysates thereof, pectins and/or hydrolysates thereof.

The effect of N-acetylneuraminic acid in the composition of the present invention was found to be essentially dose dependent. Small amounts will produce smaller effects and large amounts may be to large so that the body cannot utilize all N-acetylneuraminic acid provided. The exact amount of N-acetylneuraminic acid to be provided will depend on the subject to be treated and on its condition, for example. While in generally every amount of N-acetylneuraminic acid will produce a beneficial effect it was found to be in particularly preferred if the N-acetylneuraminic acid is present in the composition in an amount of 1 mg-250 mg/g dry mass of the composition.

The N-acetylneuraminic acid may be administered in a daily amount of 1 mg-2 g/kg body weight, preferably 0.025 g to 0.8 g/kg body weight of the subject to be treated.

Those skilled in the art will understand that they can freely combine all features of the present invention described herein, without departing from the scope of the invention as disclosed. In particular, features described for the uses of the present invention may be applied to the composition of the present invention and vice versa.

Further advantages and features of the present invention are apparent from the following Examples and Figures.

FIGURES

EXAMPLES

Figure 1:
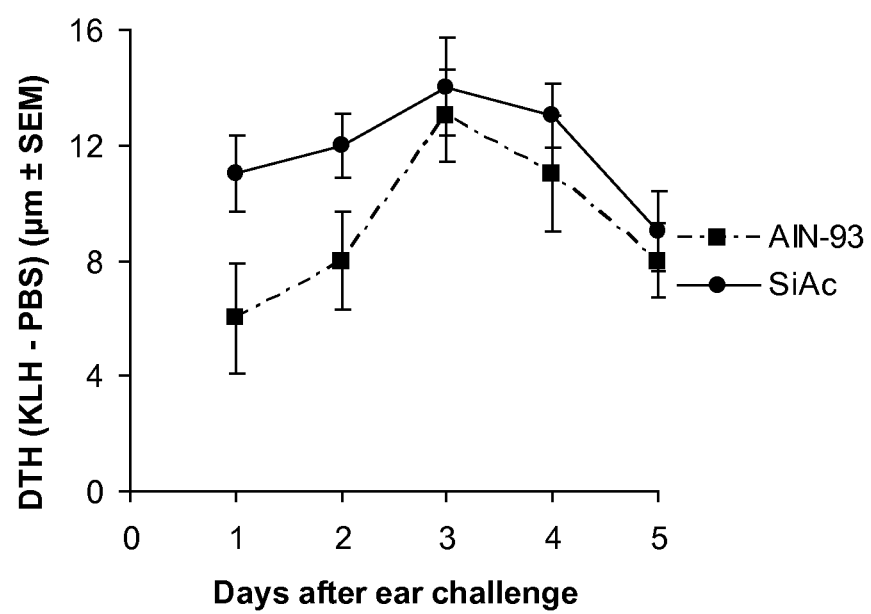
FIG. 1 shows the cell-mediated immune delayed-type hypersensitivity (DTH) response in aged mice non-supplemented (AlN-93, n=10) or supplemented with SiAc (SiAc, n=10).

Ageing is associated with a dysregulation of the immune system, such as a noted decline in cell-mediated immune response concomitant with an increased humoral immune dysfunction (e.g. lower response to vaccine). Ageing is furthermore often associated with a status of low-grade inflammation and of increased oxidative stress. Consequently, in particular many elderly subjects are at increased risk of infectious and non-infectious diseases that contribute to morbidity and mortality.

Study Design for Assessing Immune Modulation in Aged Mice

Specific pathogen-free male C57BL/6J mice (4-weeks old) were purchased from Janvier (France). Mice were housed under conventional circumstances (12 hours light/dark cycle, temperature 22° C., humidity 56%) and received water and semi-synthetic Kliba 3436 diet ad libitum. Until the age of 5 months, mice were maintained at 5 per cage and then they were individually caged. All conditions and handling of the animals were approved by the Nestle and state ethical committees with the agreement of the Swiss Federal Veterinary Advisor. 19-months old mice were randomized into 2 groups of 10 animals and were fed with a semi-synthetic AlN-93 diet either non-supplemented (group control AlN-93, n=10) or supplemented with SiAc (0.8 weight-% N-acetylneuraminic acid in the diet) (group SiAc, n=10). During the 42 days of trial, all mice were allowed to drink and eat ad libitum.

The DTH response was used as an in vivo measure of cellular immunity. Measurements of ear thickness (ear swelling) taken prior to, and 24 hours to 6 days following, elicitation allowed for determination of the ability to generate a DTH response. Briefly, on day 15 of the trial, mice were immunized by subcutaneous injection (100 μl) of an inert antigen Keyhole Limpet Haemocyanin (KLH, Sigma) at 100 μg in 1% Alum (Brenntag Biosector, Frederikssund, Denmark). Seven days after immunization, DTH responses were elicited by injecting the recall-antigen KLH (10 μl of 0.5 μg/ml) into each mouse's right ear. The left ears were injected with vehicle alone (saline=PBS) and served as internal controls for each animal. At 24 hours post-elicitation, and during the following 5 days, both the non-elicited (left ear) and the elicited ears (right ear) were measured. DTH responses (KLH-PBS) were expressed as the magnitude of ear swelling, i.e. the change in ear thickness using the following formula: Δ in ear thickness=[elicited ear (right, KLH) ear sickness−non-elicited (left, PBS) ear sickness], where Δ in ear thickness= [post-elicitation−pre-elicitation ear thickness].

Mice were killed on day 42 of trial. The expression of genes involved in inflammatory processes was determined in the liver of aged mice that were supplemented or not with SiAc for 42 days.

At the autopsy, the liver was removed and a piece was immediately frozen in liquid nitrogen and then stored at −80° C. until further analysis.

Liver samples were transferred into 1 ml of RNA lysis buffer (Macherey-Nagel, Düren, Germany) and homogenized using Ribolyzer (Hybaid, Waltham, Mass., USA) with the following setting: power at 6 for 20 seconds. RNA extraction was conducted using a commercially available kit (NucleoSpin RNA II Kit; Macherey-Nagel, Duren, Germany). RNA quantification was achieved using the Ribogreen RNA Quantitation Kit (Molecular Probes; Eugene, Oreg. USA), and RNA quality was assayed using Agilent RNA 6000 Nano LabChip Kit (Agilent Technologies, Palo Alto, USA). Total RNA (2 μg) was reverse transcribed using Multiscribe reverse transcriptase following manufacturer's instructions (Applied biosystems, Biosystems; Rokreutz, Switzerland).

Custom-made low density arrays (LDA) with TaqMan probes were purchased from Applied Biosystems (Foster City, USA) and used according to manufacturer instructions. Gene expression was calculated using the relative quantification method ΔΔCt method with SDS 2.2.2 software (Applied Biosystems). The resulting cycle threshold (Ct) values were exported into MS Excel (Microsoft, USA) for further analysis. Briefly, the ΔCt value (i.e. Ct value of the target gene—Ct value of the GAPDH housekeeping gene) was first calculated and then the relative mRNA expression was determined using the following formula: $2^{-\Delta Ct} \times 10^6$. Data were analyzed by means+/−SEM and the Student's T test (unpaired) or two-way ANOVA when appropriate. Probability values of less than 5% were considered as significant.

Results:
Immune Enhancing Effects of SiAc Supplementation in Aged Mice

Figure 2:
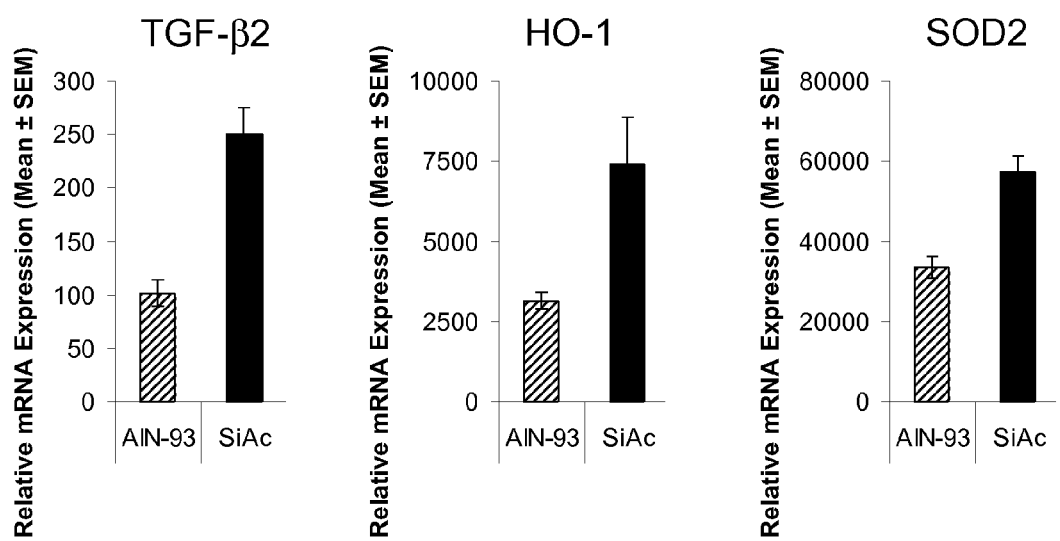
FIG. 2 shows the expression of mRNA encoding for molecules involved in anti-inflammatory process (TGF-β2) and playing a role in defence against oxidative damage (HO-1 and SOD-2) in liver of aged mice non-supplemented (AlN-93, n=8) or supplemented with SiAc (SiAc, n=8) for 42 days.

Dietary supplementation with SiAc (0.8 weight-% N-acetylneuraminic acid incorporated in the diet) improved cell-mediated immune response (FIG. 1) in aged mice. This supplementation alleviates age-related low-grade inflammation and oxidative damage (FIG. 2), as observed by increased expression of genes encoding for an anti-inflammatory molecule (e.g. TGF-β2) or for molecules involved in the defence against oxidative damage (e.g. HO-1 and SOD2).

The invention claimed is:

1. A method for treating a disorder linked to an alteration of the immune system selected from the group consisting of infections, autoimmune-like diseases, innate defence disorders, cyclic neutropenia, and combinations thereof, the method comprising administering a therapeutically-effective amount of a composition containing a protein fraction comprising N-acetylneuraminic acid bound to a threonine rich peptide/protein backbone to an individual having same, the protein fraction comprises at least one glycosylated amino acid or peptide selected from the group consisting of NeuAc-α-2,3-Gal-β-1,3-(NeuAc-α-2,6-)-GalNAc-$R_n$, NeuAc-α-2,3-Gal-β-1,3-GalNAc-$R_n$, Gal-β-1,3-(NeuAc-α-2,6-)-GalNAc-$R_n$, and Gal-β-1,3-GalNAc-$R_n$, wherein R is an amino acid residue and n has a value between 1 and 10; if n has a value of 1, R is a threonine residue or a serine residue; and if n has a value of 2 to 10, the peptide contains at least one threonine or serine residue, and at least 15 mol % of the ingredient is N-acetyl-neuraminic acid.

2. The method of claim 1, wherein the protein fraction comprises about 7 to 25% by weight N-acetylneuraminic acid and threonine in an amount of between about 8 and 22% of the total number of amino acids.

3. The method of claim 1 wherein the disorder is linked to an impaired cell mediated immune response.

4. The method of claim 1, wherein the alteration of the immune system is selected from the group consisting of infections, innate defence disorders, cyclic neutropenia; and combinations thereof.

5. The method of claim 1 for producing a vaccine response stimulating effect.

6. The method of claim 1, wherein the composition treats infectious diseases.

7. The method of claim 1, wherein the composition is in a form selected from the group consisting of a pharmaceutical composition, and a food product.

8. The method of claim 1, wherein the composition comprises an ingredient selected from the group consisting of another immune boosting agent and a probiotic.

9. The method of claim 1, wherein the composition comprises a fraction selected from the group consisting of a fat fraction and a carbohydrate fraction.

10. The method of claim 1, wherein the composition comprises an ingredient selected from the group consisting of a pain relieving agent, a stabilizing agent, a flavouring agent, a colouring agent, a lubricant, and a prebiotic.

11. The method of claim 1, wherein the composition is intended for humans or pets.

12. The method of claim 1, wherein the N-acetylneuraminic acid is present in the composition in an amount of 1 mg to 250 mg/g dry weight of the composition.

13. The method of claim 1, wherein the N-acetylneuraminic acid is to be administered in a daily amount of 1 mg to 2 g /kg body weight of the subject to be treated.

14. The method of claim 1, wherein the composition is selected from the group consisting of milk powder based products; instant drinks; ready-to-drink formulations; nutritional powders; nutritional liquids; milk-based products; cereal products;

beverages; water; coffee; cappuccino; malt drinks; chocolate flavoured drinks; culinary products;

soups; topical creams; suppositories; tablets; syrups, and formulations for transdermal applications.

15. The method of claim 1 to be administered to the elderly.

16. The method of claim 1, comprising co-administering the composition with a vaccine.

* * * * *